United States Patent [19]
Nonomura et al.

[11] Patent Number: 5,958,104
[45] Date of Patent: Sep. 28, 1999

[54] METHODS AND COMPOSITIONS FOR ENHANCING PLANT GROWTH

[76] Inventors: Arthur M. Nonomura, 311 Depot Rd., Boxborough, Mass. 01719; Andrew A. Benson, 6044 Folsom Dr., La Jolla, Calif. 92037

[21] Appl. No.: 08/928,068

[22] Filed: Sep. 11, 1997

[51] Int. Cl.⁶ ............................. C05F 5/00; C05F 11/00
[52] U.S. Cl. ............................ 71/11; 71/26; 504/118; 504/123; 504/189
[58] Field of Search ........................... 71/11, 27, 28, 71/29, 26; 504/118, 189, 123; 514/24, 25, 42, 53, 54

[56] References Cited

U.S. PATENT DOCUMENTS

| | | | |
|---|---|---|---|
| H303 | 7/1987 | Malik et al. | 514/85 |
| 4,242,120 | 12/1980 | Manankov | 71/89 |
| 4,301,251 | 11/1981 | Rumyantseva et al. | 435/267 |
| 4,348,424 | 9/1982 | Consolazio et al. | 427/4 |
| 4,383,845 | 5/1983 | Rutherford | 71/16 |
| 4,449,997 | 5/1984 | Iwamura et al. | 71/88 |
| 4,482,537 | 11/1984 | El-Menshawy et al. | 424/59 |
| 4,556,505 | 12/1985 | Fenn | 252/194 |
| 4,652,636 | 3/1987 | Drewes et al. | 536/4.1 |
| 4,764,201 | 8/1988 | Iino et al. | 71/77 |
| 4,889,877 | 12/1989 | Seitz | 523/161 |
| 5,061,697 | 10/1991 | Shasha et al. | 514/60 |
| 5,077,206 | 12/1991 | Cheetham et al. | 435/99 |
| 5,231,117 | 7/1993 | Seitz | 523/161 |
| 5,271,958 | 12/1993 | Szczepanski et al. | 427/150 |
| 5,482,639 | 1/1996 | Archer et al. | 252/70 |
| 5,514,580 | 5/1996 | Oglevee-O'Donovan et al. | 435/240.45 |
| 5,516,747 | 5/1996 | Lachut | 504/116 |
| 5,532,204 | 7/1996 | Joshi | 504/118 |
| 5,549,729 | 8/1996 | Yamashita | 71/26 |
| 5,597,400 | 1/1997 | Nonomura et al. | 71/28 |
| 5,750,513 | 5/1998 | Hoorne et al. | 514/54 |

FOREIGN PATENT DOCUMENTS

| | | | |
|---|---|---|---|
| 0 063 194 A1 | 10/1982 | European Pat. Off. | A01N 45/00 |
| 0 275 005 B1 | 7/1988 | European Pat. Off. | C07F 9/10 |
| 0 364 202 A2 | 4/1990 | European Pat. Off. | A01N 57/20 |
| 0 402 637 B1 | 4/1991 | European Pat. Off. | B41M 5/155 |
| 0 439 874 B1 | 8/1991 | European Pat. Off. | C09D 11/02 |
| 0 498 145 B1 | 8/1992 | European Pat. Off. | A01N 57/20 |
| 0 590 538 B1 | 4/1994 | European Pat. Off. | A61K 7/00 |
| 0 650 365 B1 | 5/1995 | European Pat. Off. | A61K 35/78 |

OTHER PUBLICATIONS

Boyd, C.A.A., "Studies on Amino Acid Inhibition of Monsaccharide Exit from Anuran Small Intestinal Epithelium" *J. Physiol.* 294:195–210 (1979).

Clayton, R.A. et al., "The first genome from the third domain of life" *Nature* 387:459–462 (May 29, 1997).

Fung, I., "A greener north" *Nature* 386:659–660 (Apr. 17, 1997).

Halkier, B.A., "Characterization of Cytochrome $P450_{TYR}$, A Multifunctional Haem–Thiolate N–Hydroxylase Involved in the Biosynthesis of the Cyanogenic Glucoside Dhurrin" *Drug Metabolism and Drug Interactions* 12(3–) :285–297 (1995).

Hara, Y. et al., "Effect of Gibberellic Acid on Berberine and Tyrosine Accumulation in *Coptis japonica*" *Phytochem.* 36(3) :643–646 (1994).

Sibbesen, O. et al., "Cytochrome $P450_{TYR}$ is a Multifunctional Heme–Thiolate Enzyme Catalyzing the Conversion of L–Tyrosine to p–Hydroxyphenylacetaldehyde Oxime in the Biosynthesis of the Cyanogenic Glucoside Dhurrin in *Sorghum bicolor* (L.) Moench" *J. Biol. Chem.* 270(8) :3506–3511 (1995).

Wachtveitl, J. et al., "Tyrosine 162 of the Photosynthetic Reaction Center L–Subunit Plays a Critical Role in the Cytochrome $c_2$ Mediated Rereduction of the Photooxidized Bacteriochlorophyll Dimer in *Rhodobacter sphaeroides*" *Biochem.* 32(40) :10894–10904 (1993).

Weber, M.J. et al., "Molecular events leading to enhanced glucose transport in *Rous sarcoma* virus–transformed cells" *Fed. Proc.* 43(8) :2246–2250 (1984).

Ichimura, K. et al., "Identification of Methyl β–Glucopyranoside and Xylose as Soluble Sugar Constituents in Roses," *Biosci. Biotech. Biochem.* 61(10) :1734–1735 (1997).

*Primary Examiner*—Wayne Langel
*Assistant Examiner*—Milan M Vinnola
*Attorney, Agent, or Firm*—Nields, Lemack & Dingman

[57] ABSTRACT

The present invention provides methods for treating plants, and for enhancing the growth of plants. The methods include applying an alkyl glucoside compound to the plant. The present invention also includes compositions useful in these methods.

21 Claims, No Drawings

METHODS AND COMPOSITIONS FOR ENHANCING PLANT GROWTH

BACKGROUND OF THE INVENTION

The present invention relates to methods and compositions for treating plants, and for enhancement of plant growth and crop yield.

Sugar has been applied to plants for tissue culture and for experimental purposes in the laboratory, but field application to plants is impractical. One of the primary limitations preventing crop application is that commonly applied sugars such as sucrose are not efficiently transported across plant cell membranes. As a result, sugar residues often remain on leaf surfaces. It would be beneficial to provide compositions for plant treatment for which membrane transport systems exist, which would enable the compositions to be absorbed by the plant and avoid the residues which result from the application of, for example, sugar.

Various higher order glucosides have been applied to plants or plant tissues. For example, U.S. Pat. No. 5,514,580 proposes benzylglucosides for propagating tissue cultures of geranium. U.S. Pat. No. 4,449,997 proposes diterpene glucosides for plant growth regulation. U.S. Pat. No. 4,764,201 proposes vitamin K derivatives including menadiol bis (glucoside tetraacetate) for accelerating plant growth. European Patent Publication No. 0 498 145 B1 proposes combinations of glyphosate herbicides with surfactant $C_{8-10}$ alkyl glycosides or alkyl polyglycosides. U.S. Statutory Invention Registration No. H303 proposes 2-ethylhexylglucoside as a pesticidal dispersing agent.

SUMMARY OF THE INVENTION

As a first aspect, the present invention provides a method for treating a plant. The method comprises applying to the plant a compound selected from the group consisting of $C_1$–$C_7$ alkyl glucosides, ether derivatives of $C_1$–$C_7$ alkyl glucosides, and combinations thereof.

As a second aspect, the present invention provides a method for enhancing growth of a plant. The method comprises applying to the plant a compound selected from the group consisting of $C_1$–$C_7$ alkyl glucosides, ether derivatives of $C_1$–$C_7$ alkyl glucosides, and combinations thereof.

As a third aspect, the present invention provides a method for treating fruit. The method comprises applying to the fruit a compound selected from the group consisting of $C_1$–$C_7$ alkyl glucosides, ether derivatives of $C_1$–$C_7$ alkyl glucosides, and combinations thereof.

As a fourth aspect, the present invention provides a composition for enhancing the growth of a plant. The composition comprises a compound selected from the group consisting of $C_1$–$C_7$ alkyl glucosides, ether derivatives of $C_1$–$C_7$ alkyl glucosides, and combinations thereof, and agronomically suitable additives.

These and other aspects of the present invention are described further in the description of the preferred embodiments and examples of the invention which follow.

DESCRIPTION OF THE PREFERRED EMBODIMENT

According to the present invention, methods and compositions are provided for treating plants and for enhancing growth of plants.

Unless otherwise defined, all technical and scientific terms employed herein have their conventional meaning in the art. As used herein, the following terms have the meanings ascribed to them.

"Enhance(s) growth" or "enhancing growth" refers to promoting, increasing or improving the rate of growth of the plant or increasing or promoting an increase in the size of the plant.

"Plants" refers to virtually all live species with active light-gathering surfaces capable of receiving treatments, particularly higher plants that fix carbon dioxide.

"Surfactant" refers to surface-active agents, which modify the nature of surfaces, often by reducing the surface tension of water. They act as wetting agents, dispersants, or penetrants. Typical classes include cationic, anionic (e.g., alkylsulfates), nonionic (e.g., polyethylene oxides) and ampholytic surfactants. Soaps, alcohols, and fatty acids are other examples.

"Ether derivative" or "alcohol derivative" refers to a derivative of the parent compound, the derivative having an ester or alcohol group covalently attached to the parent compound. A representative example of a parent compound and an ether derivative thereof is methyl glucoside and its ether derivative polyethyleneglycol (PEG) methyl glucoside.

"Percent" or "%" is percent by weight unless otherwise indicated.

"ppm" refers to parts per million by weight.

"Alkyl" refers to linear or branched, saturated or unsaturated $C_1$–$C_7$ hydrocarbons. Examples of alkyl groups include methyl, ethyl, ethenyl, propyl, propenyl, isopropyl, butyl, isobutyl, t-butyl, pentyl, hexyl, and the like.

"Growing media" refers to any agronomically suitable media in which plants may be cultivated. Examples include any of various media containing agronomically suitable components (e.g., sand, soil, vermiculite, peat); agar gel; and any of various hydroponic media, such as water, glass wools or PERLITE®.

"Oxidant" refers to electron acceptors or reductase substrates that induce NADPH:Cytochrome P450 Reductase (CPR). Reductase substrates which induce CPR accelerate the metabolism of reductants by Cytochromes P450 monooxygenase(CYP).

"Reductant" refers to electron donor or oxidase substrates that induce CYP. Oxidase substrates which induce CYP accelerate the metabolism of oxidants by CPR.

"Aqueous" with reference to solutions or solvents refers to solutions or solvents which consist primarily of water, normally greater than 90 weight percent water, and can be essentially pure water in certain circumstances. For example, an aqueous solution or solvent can be distilled water, tap water, or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith. Agronomically suitable organic solvents include, for example, paraffin oil, acetone, emulsifiers and polysiloxanes.

The compositions and methods of the present invention may be applied to virtually any variety of plants and fruits. In particular, the compositions and methods of the present invention may be advantageously applied to "higher plants." Higher plants include, but are not limited to all species having true stems, roots, and leaves, thus excluding "lower plants" such as bacteria, yeasts and molds. Plants which may benefit according to the present invention include but are not limited to all crop plants, such as, alfalfa, anise, bach ciao, barley, basil, blueberry, breadfruit, broccoli, brussels sprouts, cabbage, cassava, cauliflower, celery, cereals, cilantro, coffee, corn, cotton, cranberry, cucumber, dill, eggplant, fennel, grape, grain, garlic, kale, leek, legume, lettuce, mint, mustard, melon, oat, onion, parsley, peanut, pepper, potato, saffron, squash, millet, parsnip, peppermint, pumpkin, radish, rice, sesame, sorghum, soy, spinach, squash, stevia, strawberry, sunflower, sweet potato, sugar beet, sugar cane, tea, tobacco, tomato, turnip, wheat, yam, zucchini and the like; pomes and other fruit-bearing plants, such as, apple, avocado, banana, breadfruit, cherry, citrus, cocoa, fig, guava, macadamia, mango, mangosteen, nut, olive, papaya, passion fruit, pear, pepper, plum, peach and the like; floral plants, such as achillea, ageratum, alyssum, anemone, aquilegia, aster, azalea, begonia, bird-of-paradise, bleeding heart, borage, bromeliad, bougainvillea, buddlea, cactus, calendula, camellia, campanula, carex, carnation, celosia, chrysanthemum, clematis, cleome, coleus, cosmos, crocus, croton, cyclamen, dahlia, daffodil, daisy, day lily, delphinium, dianthus, digitalis, dusty miller, euonymus, forget-me-not, fremontia, fuchsia, gardenia, gazania, geranium, gerbera, gesneriad, ginkgo, gladiolus, hibiscus, hydrangea, impatiens, jasmine, lily, lilac, lisianthus, lobelia, marigold, mesembryanthemum, mimulus, myosotis, New Guinea Impatiens, nymphaea, oenothera, oleander, orchid, oxalis, pansy, penstemon, peony, petunia, poinsettia, polemonium, polygonum, poppy, portulaca, primula, ranunculus, rhododendron, rose, salvia, senecio, shooting star, snapdragon, solanum, solidago, stock, ti, torenia, tulip, verbena, vinca, viola, violet, zinnia, and the like; leafy plants, such as ficus, fern, hosta, philodendron, and the like; trees, such as Abies, birch, cedar, Cornus, cypress, elm, ficus, fir, juniper, magnolia, mahogany, maple, oak, palm, Picea, Pinus, Pittosporum, Plantago, poplar, redwood, Salix, sycamore, Taxus, teak, willow, yew, Christmas tree and the like; grasses, such as Kentucky blue grass, bent grass, turf, festuca, pennisetum, phalaris, calamogrostis, elymus, helictotrichon, imperata, molina, carex, miscanthus, panicum, and the like; and thalloid plants such as algae, and seaweeds such as kelp, Eucheuma, laver, nori, kombu and wakame. This list is intended to be exemplary and is not intended to be exclusive. Other plants which may benefit by application of the compositions and methods of the present invention will be readily determined by those skilled in the art.

The alkyl glucosides which are the subject of the present invention are currently believed to function in a manner similar to conventional fertilizers. The methods and compositions of the present invention may be used to enhance growth in juvenile and mature plants, as well as cuttings and seeds. Generally, however, it is desirable that the plants include at least the sprouted cotyledon (i.e., the "seed leaves") or other substantial light-gathering surfaces including the true leaves. Fruit bearing plants may be treated before and after the onset of bud, fruit and seed formation.

The compositions of the present invention penetrate into photosynthetic plants, providing a substrate for growth. Unlike sugars, membrane transport systems exist for the alkyl glucosides employed in the compositions and methods of the present invention. Carbon fixation in a leaf is enhanced by focusing on direct input by application of alkyl glucosides to whole plants or to any plant part. Input of the alkyl glucosides into plant roots and shoots allows increased capacity for turgidity and growth, particularly when applied together with conventional fertilizers and/or agronomically suitable additives to support metabolic functions.

The methods of the present invention, for the treatment of plants and for the enhancement of growth in plants are carried out by applying to the plant an alkyl glucoside, or a hydrate thereof or ester derivative thereof. Suitable alkyl glucosides for use in the methods and compositions of the present invention include the $C_1$–$C_7$ alkyl glucosides as well as any of a wide variety of glucoside derivatives including but not limited to ethoxylate derivatives, propoxylate derivatives, salts, hydrates, aldehyde derivatives, ester derivatives, ether derivatives, alcohol derivatives, phenol derivatives, amine derivatives, other biologically or chemically equivalent substances, and any combination of two or more of the foregoing. We have found that the lower chain glucosides are advantageously absorbed and metabolized by the plant through the existing membrane transport systems. More specifically, suitable alkyl glucosides include methyl glucoside compounds such as α-methyl glucoside, β-methyl glucoside, and combinations thereof; ethyl glucoside; and propyl glucoside. Suitable ether derivatives of alkyl glucosides include but are not limited to polyethyleneglycol methyl glucoside ether (PEG-methyl glucoside ether) and polypropyleneglycol methyl glucoside ether (PPG-methyl glucoside ether). Any two of the foregoing alkyl glucosides may be combined for use in the methods and compositions of the present invention. Currently, the preferred alkyl glucosides for use in the methods and compositions of the present invention include a-methyl glucoside, β-methyl glucoside, combinations of α- and β-methyl glucoside, PEG-methyl glucoside ether and PPG-methyl glucoside ether. α-Methyl glucoside is currently the most preferred alkyl glucoside for use in the methods and compositions of the present invention.

Although the alkyl glucoside compound may be applied to the plant in a solid form, it is often advantageous to provide the alkyl glucoside in liquid form, such as by dispersing, solubilizing, or otherwise admixing the alkyl glucoside in an aqueous or agronomically suitable organic solvent or carrier to produce aqueous or organic solutions, dispersions or emulsions containing the alkyl glucoside for application to the plant. The amount of alkyl glucoside which is solubilized in the carrier will depend upon the particular alkyl glucoside selected and the method of application. The alkyl glucoside compound may be solubilized in the carrier by adding the compound to the carrier and allowing the compound to dissolve. In some instances, the application of stirring, agitation, or even heat may facilitate the dissolution of the alkyl glucoside in the carrier. Typically, the alkyl glucoside is included in the aqueous or organic solution at a concentration of between about 0.05% by weight and about 25% by weight inclusive, preferably between about 0.1% and about 20% by weight. Aqueous solutions of the alkyl glucoside are preferred. For example, the alkyl glucosides are typically applied to roots or shoots as an aqueous solution at a concentration in the range from about 0.1% to 20%, preferably from about 0.1% to 3%.

The alkyl glucoside compounds employed in the methods of the present invention may be applied to the plants using conventional application techniques. Plants nearing or at maturity may be treated at any time before and during seed development. Fruit bearing plants may be treated before or after the onset of bud or fruit formation. Improved growth occurs as a result of the exogenus application of alkyl glucoside.

The alkyl glucoside compounds employed in the present invention may be applied to the plant at a location including leaves, shoots, root, seed, stem, flowers, and fruit. The compounds may be applied to the leaves, seed or stem by spraying the leaves with the solution containing the alkyl glucoside. The compound may be applied to the shoot or root by spraying the shoot or root, or dipping the shoot or root in a bath containing the alkyl glucoside (preferably in the form of a solution), or drenching the growing medium in which the plant is being cultivated with the solution containing the alkyl glucoside, or spray-drenching the leaves and stem of the plant such that the growing medium in which the plant is being cultivated becomes saturated with the solution containing the alkyl glucoside. Side dressing is also applicable.

Foliar application (i.e., application to one or more leaves of the plant) in combination with root application of the alkyl glucoside is one preferred application method. Currently, the most preferred methods of application are the root application and spray-drenching application. The alkyl glucoside will normally be applied to the leaves of the plant using a spray. However, other means of foliar application such as dipping, brushing, wicking, misting, electrostatic dispersion and the like of liquids, foams, gels and other formulations may also be employed. Foliar sprays can be applied to the leaves of the plant using commercially available spray systems, such as those intended for the application of foliar fertilizers, pesticides, and the like, and available from commercial vendors such as FMC Corporation, John Deere, Valmont and Spraying Systems (TEEJET®). If desired, oxidant and reductant compounds may be applied to plants in rapid sequence from separate nozzles in separate reservoirs. Chemically compatible combined mixtures may be preferred for many applications to produce improved plant growth.

In the embodiment wherein the root and/or shoot is dipped in a bath containing the alkyl glucoside, it is preferred to pulse the application of the alkyl glucoside by dipping the shoot and/or root in the bath containing the alkyl glucoside for a period of time and then removing the shoot and/or root from the bath. The dipping period may be from 1 minute to 60 minutes, and is preferably from 10 to 30 minutes.

The alkyl glucoside may also be applied to plant tissues, such as cell suspensions, callus tissue cultures, and micropropagation cultures. Such plant tissues may be treated with the alkyl glucoside by adding the compound to the culture medium in which the plant tissues are being cultivated.

In the methods of the present invention, the alkyl glucoside is typically applied to the plant or fruit at a concentration ranging from about 0.01% by weight to about 100% by weight. Shoot applications will preferably be in the range from 0.3% to 3% by weight. Hydroponic applications will preferably be in the range of 0.3% to 1.2%, preferably by a pulsed exposure for up to an hour. Foliar applications of shoots by tractor overhead spray booms over crop rows will preferably be in the range of 5 to 25 pounds per acre. Root applications by side dressing into soil near the root zone will preferably be in the range of 10 to 100 pounds per acre. Ornamentals and other tender nursery plants meant for indoor horticulture will frequently require lower concentrations and perhaps more frequent application than outdoor agricultural crops.

The solutions containing the alkyl glucoside may also include any of a wide variety of agronomically suitable additives, adjuvants, or other ingredients and components which improve or at least do not hinder the beneficial effects of the alkyl glucoside (hereinafter "additives") to provide the compositions of the present invention. Generally accepted additives for agricultural application are periodically listed by the United States Environmental Protection Agency. For example, foliar compositions may contain a surfactant and a spreader present in an amount sufficient to promote wetting, emulsification, even distribution and penetration of the active substances. Spreaders are typically organic alkanes, alkenes or polydimethylsiloxanes which provide a sheeting action of the treatment across the phylloplane. Suitable spreaders include paraffin oils and polyalkyleneoxide polydimethylsiloxanes. Suitable surfactants include anionic, cationic, nonionic, and zwitterionic detergents, amine ethoxylates, alkyl phenol ethoxylates, phosphate esters, PEG, polymerics, polyoxyethylene fatty acid esters, polyoxyethylene fatty diglycerides, sorbitan fatty acid esters, alcohol ethoxylates, sorbitan fatty acid ester ethoxylates, ethoxylated alkylamines, quaternary amines, sorbitan ethoxylate esters, alkyl polysaccharides, block copolymers, random copolymers, trisiloxanes, CHELACTANTS™ and blends. Surfactant preference is for polyalkylene oxides, polyalkylene glycols, and alkoxylate-fatty acids. Blends are highly effective such as our organosiloxane/nonionic surfactant SILWET® Y14242 (Y14242) blend which use is demonstrated in our examples. Preferred commercial aqueous surfactants include Hampshire LED3A; HAMPOSYL®; TEEPOL®; TWEEN®; TRITON®; LATRON™; PLURONIC®; TETRONIC®; SURFONIC®; SYNPERONIC®; ADMOX®; DAWN®, and the like. Commercial emulsifiers for combination with organic solvent formulations include WITCANOL®, RHODASURF®, TERGITOL® and TWEEN®. Commercial spreaders include TEGOPREN®, AGRIMAX™, DOW CORNING® 211, X-77®, SILWET® and the like. Penetrants such as sodium dodecylsulfate, formamides and lower aliphatic alcohols, may be used. Alkoxylation of an active component or otherwise chemically modifying the active components by incorporating a penetrant substance is useful because formulation without additional surfactant is achieved.

In addition to the foregoing additives, the compositions of the present invention may also advantageously include one or more conventional fertilizers. Suitable fertilizers for inclusion in the compositions, methods and systems of the present invention will be readily determinable by those skilled in the art and include conventional fertilizers containing elements such as nitrogen, phosphorus, potassium, elevated carbon dioxide, hydrogen peroxide and the like. Phosphorous, potassium, and nitrogenous fertilizers (i.e., fertilizers containing nitrogen) are currently preferred, particularly nitrate or ammonia fertilizers and salts thereof. In particular, in cases requiring foliar fertilizers, nitrate fertilizers are most preferred. In order to support rapid vegetative growth above normally fertilized crops, the most highly preferred fertilizer for inclusion in methyl glucoside formulations are nitrogenous fertilizers, especially nitrate, urea, and ammonium salts, within the supplemental range of 0.2% to 2%. For example, 1% to 3% methyl glucosides are formulated with the nitrogen source, 0.2% to 0.6% ammonium nitrate. Variations in the compositions may be made for enhancement of flowering and pigmentation by adjusting the N-P-K ratios, for instance, reduction of N and enhancement of P by adding phosphate buffers such as $KH_2PO_4$ and $K_2HPO_4$ will intensify flowering.

The amount of fertilizer added to the compositions of the present invention will depend upon the plants to be treated, and the nutrient content of the soil. Generally, fertilizers will be present in amounts sufficient to balance growth attained with alkyl glucoside when applied to the plant. Typically, the conventional fertilizer is included in the amount of between about 10 ppm and about 1000 ppm, preferably between about 50 ppm and about 900 ppm, and more preferably between about 60 ppm and about 600 ppm by weight of the composition. High potency is achieved by shoot or root application of formulations which provide the methyl glucoside in combination with conventional plant nutrients or readily metabolized precursors, thereto.

The compositions of the present invention may also include any of various secondary nutrients, such as sources of sulfur, calcium, and magnesium; as well as micronutrients, such as chelated iron, boron, cobalt, copper, manganese, molybdenum, zinc, nickel, and the like, which are conventionally formulated in foliar fertilizers. Other conventional fertilizer constituents which may be added to the compositions of the present invention include pesticides, fungicides, antibiotics, plant growth regulators, gene therapies and the like.

Among the plant growth regulators which may be added to the compositions of the present invention are auxins; brassinolides; cytokinins; gibberellins; amino acids; benzoates; vitamins; herbicides, such as, phosphonomethylglycine and sulfonylurea; salts, esters, phosphates, hydrates and derivatives thereof; and the new cytochrome P450 plant growth regulating compositions which are the subject of copending U.S. patent application Ser. No. 08/927,415, pending, filed concurrently herewith in the name of the presently named inventors, the disclosure of which is incorporated herein by reference in its entirety.

Briefly, the cytochrome P450 plant growth regulating compositions comprise: (a) an aqueous solution containing an amount of a first component selected from the group consisting of (i) NADPH:cytochrome P450 reductase enzyme and (ii) oxidants which induce NADPH:cytochrome P450 reductase in the plant, and (b) an aqueous solution containing an amount of a second component selected from the group consisting of (i) cytochrome P450 monooxygenase enzyme and (ii) reductants which induce cytochrome P450 monooxygenase in the plant.

Suitable oxidants for use as the first compound of the composition include but are not limited to reductases such as cytochrome P450 reductase enzyme, NADPH, NADP, NADH, and NAD; flavins such as flavin mononucleotide (FMN), flavin adenine dinucleotide (FAD), deazaflavin, riboflavin, lumichrome, lumizine, alloxazine, and manganese; nitrobenzoate compounds such as p-nitrobenzoate, polyethylene glycol nitrobenzoate, and nitrophenolate; nitrobenzoic acid compounds such as m-nitrobenzoic acid, p-nitrobenzoic acid (pNBA), 4-chloro-2-nitrobenzoic acid, and 2-chloro-4-nitrobenzoic acid; haloaryl compounds such as iodobenzoate; amine oxides such as tertiary amine-N-oxide; carbamates such as N-(3, 4-methylenedioxyphenyl) carbamates; glycolates and glycolic metabolites such as glycolate, potassium glycolate, glycolic acid, and formate; cytochrome reductases such as cytochrome f, cytochrome c, cytochrome b5, flavocytochrome P450, nitric oxide synthase, and cytochrome P450 tyrosine; azo compounds such as diazolidinylurea, azodicarboxamide; quinone compounds such as anthraquinone sulfonate; bipyridinium compounds such as bis(dimethylaminocarbonyl) propylbipyridinium, and ethylpropenylmethoxyethylbipyridinium; and all salts, hydrates, aldehydes, esters, amines, surfactant-linked derivatives, and other biologically or chemically equivalent derivatives thereof, and combinations of any two or more of the above thereof. Preferred oxidant compounds exhibit a one electron reduction potential ($E_o$) between about −400 mV and about −165 mV inclusive, more preferably between about −396 mV and about −240 mV.

Currently preferred oxidants for use as the first compound in the plant growth regulating compositions include but are not limited to FAD, FMN, pNBA, glycolate, and salts, hydrates and surfactant-linked derivatives thereof. FMN is a particularly preferred oxidant.

Suitable reductants for use as the second compound of the composition include but are not limited to cytochromes such as cytochrome P450 tyrosine and hemoglobin; amines such as tyrosine, tyrosine ester, tyrosine methylester, tyrosine methylester hydrochloride, tyramine, alanyltyrosine, levodopa, aminopyrine, and phosphonomethylglycine; cinnamates such as trans-cinnamic acid; orcinols such as resorcinol; salicylates such as aspirin; retinoids such as trans-retinoic acid; fatty acids such as lauric acid, palmitic acid, arachidonic acids, and linoleic acid; pteridines such as m-aminobenzoic acid, p-aminobenzoic acid, and PEG-25 p-aminobenzoic acid; tetrahydrofolates such as tetrahydrobiopterin; alcohols such as methanol, ethanol, and phenol; ketones such as acetone; pyridine; formamidines such as formamidine and formamidine acetate; indoles such as indole-3-glycerol phosphate and indole-3-acetic acid; brassinolides; barbiturates such as phenobarbital; flavones such as isoflavone; and all salts, hydrates, aldehydes, esters, amines, surfactant-linked derivatives, and other biologically or chemically equivalent derivatives thereof and combinations of any two or more of the above. Preferred reductants include, but are not limited to those electron donors with a reduction potential ($E_o$) between about 1 and about 2000 mV, and more preferably between about 600 mV and about 900 mV.

Currently preferred reductants for use in the plant growth regulating compositions include but are not limited to tyrosine methylester, tyrosine methylester hydrochloride, aminopyrine, p-aminobenzoic acid, and PEG-25 p-aminobenzoic acid.

Currently preferred plant growth regulating compositions including but are not limited to glycolate together with p-aminobenzoic acid or PEG-25 p-aminobenzoic acid; p-nitrobenzoic acid together with p-aminobenzoic acid or PEG-25 p-aminobenzoic acid; p-nitrobenzoic acid together with tyrosine, tyrosine ester, tyrosine methylester, or tyrosine methylester hydrochloride; flavin mononucleotide together with p-aminobenzoic acid or PEG-25 p-aminobenzoic acid; and flavin mononucleotide together with tyrosine, tyrosine ester, tyrosine methylester, or tyrosine methylester hydrochloride.

Typically, the oxidant and reductant are provided in solution wherein the concentration of the oxidant is in the range between about 0.0001% and about 1% by weight of the composition inclusive, preferably between about 0.01% and about 0.5% inclusive; and the concentration of the reductant is in the range between about 0.0001% and about 10% by weight of the composition inclusive, preferably between about 0.01% and about 0.3% inclusive.

In the methods of the present invention, the compositions are typically applied in the amount of between about 3 gallons per acre and about 200 gallons per acre, depending upon the application method. For horticulture applications, the compositions are preferably applied in the amount of between about 75 gallons per acre and about 125 gallons per acre. For ground rig row crop applications, the compositions are preferably applied in the amount of between about 10 gallons per acre and about 40 gallons per acre. For aerial applications by helicopter or airplane crop dusters, the compositions are preferably applied in the amount of between about 1 gallon per acre and about 5 gallons per acre. The compositions may be applied in a single application or in multiple applications interrupted by a period of photosynthetic activity. Ornamentals and other tender nursery plants meant for indoor horticulture will frequently require lower concentrations and perhaps more frequent application than outdoor agricultural crops.

Throughout the growing season, the plant will be fed fertilizers sufficient to promote optimal growth. In cases requiring nitrogen fertilizers, nitrates an ammoniacal nitrogen are recommended. In general agricultural practice, withholding pesticidal treatment of the crop for at least 1 day prior to and following treatment with alkyl glucoside is recommended to prevent interference. Suitable light and temperature conditions may be achieved by treating plants at any time of day or night. Optimal to hot temperatures, usually above 15° C. and preferably above 25° C., are required after treatment.

After treatments, either sun or artificial illumination should have an intensity and duration sufficient for prolonged high rates of photosynthesis throughout the growing season. Suitable illumination intensities lie between 400 $\mu$mol and 2000 $\mu$mol photosynthetically active quanta (400–700 nm) m$^{-2}$ s$^{-1}$, with direct sunlight normally providing sufficient illumination. Prior to treatment, leaf temperature should be sufficiently high for optimal growth or hotter, usually from 10° C. to 35° C. or higher. After treatment, the leaf temperature will normally drop a few degrees as a consequence of improved photosynthetic efficiency. It is preferable that the plant be exposed to at least a week of intense illumination preferably greater than 400 $\mu$mol photosynthetically active quanta M$^2$-s$^{-1}$ following application of of the alkyl glucoside composition.

Compositions according to the present invention may be tailored for specific uses, including enhanced performance or tolerance under environmental stress; enhanced yield; optimizing growing seasons; aftermarket caretaking; flower retention; fruit optimization; and in all areas of agriculture in which optimal growth is beneficial. Alkyl glucoside compositions may be modified according to targeted natural products enhancement, stress reduction, activity enhancement of plant growth regulators, safening and general yield enhancement of crops.

The following examples are provided to illustrate the present invention, and should not be construed as limiting thereof. In these examples, glycine (gly) and purified water were obtained from Hampshire Chemical Corporation. GEO-MEG®D365 an $\alpha$-methyl glucoside: $\beta$-methyl glucoside 2:1 liquid blend ($\alpha\alpha\beta$) was obtained from Horizon Products. PELRON® PEL-RIG 9742 polyether polyol (PEG) was obtained from Pelron Corporation. Ammonium sulfate (($NH_4)_2SO_4$), $\alpha$-methyl glucoside ($\alpha$MN), potassium nitrate ($KNO_3$), and urea were obtained from Fisher Scientific. trans-Cinnamic acid (Cinnamic) and tyrosine methyl ester HCl (TyClMe) were obtained from Sigma. Methyl-$\beta$-D-glucoside was obtained from TCI America. Silwet® Y14242 (Y14242) was obtained from OSi.

GEO-MEG®365 is 65% methyl glucosides. It may be proportioned according to its content of $\alpha$-methyl glucoside to replace pure $\alpha$-methyl glucoside and vice versa. PELRON® PEL-RIG 9742 is a polyether polyol derived from GEO-MEG®365. The chemical formula "($NH_4)_2SO_4$" is ammonium sulfate and "$KNO_3$" is potassium nitrate. Typically, $KH_2PO_4$ (i.e., monopotassium phosphate) and $K_2HPO_4$ (i.e., dipotassium phosphate) were formulated as phosphate buffers to maintain pH 5.5 to pH 7.5 and to provide major nutrients as needed.

Additional abbreviations utilized in the following examples are defined as follows: "L" means liter; "ml" means milliliter; "cm" means centimeter; "cm$^2$" means centimeters squared; "nm" means nanometer; "g" means grams; "mg" means milligrams; "M" means molar; "mM" means millimolar; "nM" means nanomolar; "$\mu$M" means micromolar; "mol" means moles; "$\mu$mol" means micromoles; "mg/ml" means milligrams per milliliter; "ppm" means parts per million based on weight; "%" or "percent" means percent by weight (of the composition); "kDa" means kiloDaltons; "h" means hour(s); "min" means minute(s); "s" means second(s); "°C." means degrees Centrigrade (all temperatures are in °C., unless otherwise indicated).

EXAMPLE 1

The following are examples of specific compositions according to the present invention which may advantageously be employed in the methods of the present invention to treat plants and to enhance growth in plants. The following exemplary compositions are intended to provide further guidance to those skilled in the art, and do not represent an exhaustive listing of compositions within the scope of the present invention.

| | Concentration | |
|---|---|---|
| | Broad Range | Narrow Range |
| First Exemplary Composition | | |
| Foliar Component | | |
| Pelron ® PEL-RIG 9742 | 0.1%–10% | 0.3% to 1% |
| Buffer | pH 5–8 | pH 7 |
| Surfactant/Spreader | 50–5000 ppm | 300–3000 ppm |
| Second Exemplary Composition | | |
| Hydroponic Root Component | | |
| $\alpha$-Methyl glucoside | 0.1%–2% | 0.5% to 1% |
| Hoagland Solution | | |

Roots of the hydroponically cultured plants are misted with the 1% methyl glucoside composition once a week. Alternatively, the roots are bathed in the 1% composition for 10 minutes to 1 hour and then replaced in conventional medium without methyl glucoside.

| Third Exemplary Composition | | |
|---|---|---|
| | Concentration | |
| | Broad Range | Preferred Content |
| Foliar Component | | |
| PELRON ® PEL-RIG 9742 | 0.1%–10% | 0.3% |
| Buffer | pH 5–8 | pH 7 |
| 4-aminobenzoic acid | 0.01–1% | 0.1% |
| Surfactants/Spreaders | 0.1% to 3% | 0.1% |

Fourth Exemplary Composition
Liquid concentrate for dilution into
1 liter of water for foliar application.

| | Concentration | |
|---|---|---|
| | Grams | Range |
| Foliar Component | | |
| GEO-MEG ® 365 | 30 | 0.5–3× |
| (NH$_4$)$_2$SO$_4$ | 4 | 0.1–2× |
| KNO$_3$ | 5 | 0.1–2× |
| Buffer | pH 5–8 | pH 7 |
| Water | 59.2 | To dissolve |
| Surfactants/Spreaders | 1 | 0–10× |

Fifth Exemplary Composition
Liquid concentrate for dilution into
1 gallon of water as a foliar spray.

| Component | Grams | Range |
|---|---|---|
| PELRON ® PEL-RIG 9742 | 37.9 | 0.1–5× |
| KNO$_3$ | 18.9 | 0.1–2× |
| KH$_2$PO$_4$ | 1.1 | pH 5 to pH 8 |
| Water | 119 | To dissolve |
| Surfactants/Spreaders | 1 | 0.5–10× |

Sixth Exemplary Composition
Liquid 20× concentrate for dilution into
1 liter of water for root application.

| Root Component | Grams | Range |
|---|---|---|
| GEO-MEG ® 365 | 12 | 0.5–3× |
| KNO$_3$ | 5 | 0.1–2× |
| Water | 15 | To dissolve |

Root application is undertaken by injection of 200 ml to 500 ml of the diluted aqueous solution into 1 gallon pots of, for example, 8 inch diameter cabbage or aster. Applications may be repeated weekly.

Seventh Exemplary Composition
Liquid concentrate for root application.

| | Concentration | |
|---|---|---|
| Component | Grams | Range |
| GEO-MEG ® 365 | 30 | 0.5–3× |
| (NH$_4$)$_2$SO$_4$ | 4 | 0.1–2× |
| KNO$_3$ | 6 | 0.1–2× |
| FeEDTA | 0.1 | 0.1–3× |
| Water | 29.9 | To dissolve |

For each plant that is a minimum of 20 cm tall or wide, inject 1 to 10 grams of the liquid concentrate into the soil or plant support medium. Irrigate immediately thereafter to move the dressing into the roots for uptake.

Eighth Exemplary Composition
Plant tissue culture composition.

| | Concentration | |
|---|---|---|
| Component | Grams per liter | Range |
| α-Methyl glucoside | 1.0 | 0.5–3× |
| Sucrose | 10 | 0–3× |
| Basal Salt Mixture (e.g. Murashige and Skoog's or Gamborg's or Anderson's, and etc.) | | |
| Water | As per Basal Salt Mixture instructions. | |
| Agar | Optional | |

Plant tissue culture media may be adjusted to substitute methyl glucoside for sucrose in proportion to growth requirements.

Ninth Exemplary Composition

| | Concentration | |
|---|---|---|
| Side Dress Root Component | Proportion | Range |
| Anhydrous Methylglucoside | 10 grams | 0.5 to 2× |
| KNO$_3$ | 0.5 grams | 0.1 to 5× |
| Calcium Silicate | 0.2 grams | 0 to 3× |

A dry powder or dry pellets are produced by mixing KNO$_3$ crystals into molten methylglucoside. Further addition of calcium silicate powder into the molten homogenate sufficient to adjust flowability may be made. Extrusion of the composition may be required to form pellets followed by cooling and milling to make powders. The dry powder may be applied to chrysanthemums at a quantity of 3 grams to 5 grams applied into the media of each 6 inch to 8 inch pot, followed by irrigation sufficient to transport the methylglucoside to the roots for uptake into the plant. For side dress injection into the soil of row crops, the dry pellet composition is preferred, with application of 10 to 100 kilograms per acre, preferably 20 kilograms per acre.

EXAMPLE 2

The following example illustrates the application of numerous compositions according to the present invention to many varieties of plants. The data demonstrate the efficacy of the methods and compositions of the present invention in the treatment of plants.

Materials and Methods

1. Plants tested under controlled and greenhouse conditions for growth response included pepper cv Bell Boy, pansy cv Delta Pure White, impatiens cv Super Elfin Violet, kale cv Osaka Red and wheat var. Geneva, and, seed geranium cv Orbit Scarlet. The preferred plant varieties utilized in the standard screening assays were responsive within 3 to 7 days of treatment.

To compare the effects of treatments under controlled conditions, seeds were sown in individual 12 to 16 cm diameter plastic pots containing Metro-Mix® 350 growing medium (Grace Horticultural Products, W. R. Grace & Co., Cambridge, Mass.) or Peter's® Professional Potting Soil (Scotts-Sierra Horticultural Products Co., Marysville, Ohio) containing complete nutrient pellets (Sierra 17-6-12 Plus Minors, Grace Sierra, Milpitas, Calif.) or fertilizers based on Hoagland nutrients were added regularly as needed. Plants were cultured in greenhouses with the option of supplemental light provided by 1,000 watt metal halide arc lights (16:8h photoperiod). In research greenhouses, no special control of physical conditions was attempted, but treatments and controls being compared were made simultaneously and were subjected to identical conditions consistent with good laboratory practices. Each survey pool held 30 or more replicates per compound tested and these were matched with equal numbers of controls. Plants were generally harvested and analyzed in the vegetative stage within two weeks after treatment. Plants in individual pots received 5 ml to 15 ml of solution per treatment applied with a hand-held sprayer or with larger commercial sprayers. Plants in trays were sprayed to drip with even distribution and pressures as would be expected of commercial sprayers. Generally, individual plants received a minimum of $0.1$ ml/cm$^2$ of solution on leaves.

Root applications were undertaken by adding GEO-MEG® 365 solutions directly into support media. The volume of application was proportioned according to the volume of the container and state of maturation of the plant. Overexposure of 7 d sprouted wheat germlings to 25 ml of 3% GEO-MEG® 365 root applications resulted in damage to wheat leaf tips, therefore, dose response curves to establish safe treatment regimes were undertaken prior to treatment of plants wherein 10–15 ml of 3% GEO-MEG® 365 were found to be safe. Examples of root applications follow: (1) 200 ml of 3% GEO-MEG® 365 solution was injected into the potting medium of 1 gallon pots of ornamental kale with 8 or more fully expanded leaves; or (2) 150 grams of GEO-MEG® 365 solution plus 75 g KNO$_3$ were added to 15 liters of 10-8-22 hydroponic growth system. Plants were maintained out-of-doors with daily irrigation and fertilization as needed.

The performance of compounds was surveyed by comparing yields against untreated controls. Yields were optimized by bracketing around the following concentrations: 100 mM methyl glucoside, 50 mM nitrogen fertilizers and 6 mM PGRs in aqueous solution. Separated additive components were included as positive controls for initial tests of mixtures. As a standard procedure, 800 ppm Y14242 surfactant blend was added to foliar formulations.

For the majority of tests of productivity yield, plants were harvested within 1 week to 2 weeks of treatment. Shoots were clipped at their bases. Fresh shoot weights were taken immediately and individual plants were wrapped and placed in a drying oven (70° C.) for 72 hours. Plant dry weights were taken and recorded. Where appropriate, population data were subjected to analysis of variance and mean separation by LSD test and showed significance within 95% confidence limits, unless noted.

For application of methyl glucoside to roots, ornamental kale were grown in 10 inch plastic pots to approximately 8 inches to 12 inches in diameter. Twenty-four plants were matched for size, color and state of maturation and placed in juxtaposed rows, with 6 plants labeled for each treatment. Two hundred grams of solution were poured into each pot. Controls were provided for N and K nutrients as well as the methyl glucoside. An untreated control row was also matched for normal culture provisions out-of-doors.

Trials were undertaken in commercial nurseries to verify practical application methods and beneficial outcome of various treatments. Automated plantings and large populations in commercial settings provided uniformity of results. Plastic trays with up to 512 cells were labeled, filled with media and sown by machine. Transplants to plastic 36 to 48 cell flats were undertaken after 5 to 8 weeks of culture depending on variety and schedules. Media such as BERGER® and METRO® mixes appropriate to the plant types were used to fill cells. Commercial foliar nutrient formulas were applied manually or by automated overhead systems. Irrigation with water was supplied daily. Plants in plug trays were generally treated at emergence of the first true leaves. Treatments consisted of foliar sprays and control solutions. Untreated controls were allocated in most cases. Baselines of 100% growth were established for growth of controls as bases for comparisons against each active substance. The percentage of change in growth caused by the tested substance compared to control is presented. The control data can be back-calculated. Mixtures of active materials contained additives, therefore, laboratory controls included plants that were treated with the same adjuvants at equivalent dilutions. In commercial trials, untreated controls were maintained. Diseased or aberrant plants were eliminated prior to test. Insects were controlled by regular treatments with appropriate commercial pesticides.

Results

Plants treated with combinations of methyl glucoside, nitrogen-sources and plant growth regulators showed enhanced growth and vegetative yields as compared to controls.

Data presented in Table 1, below, compares yields of plants subjected to various treatments and untreated controls in live and dry weights and percent ratios of treated/controls.

TABLE 1

Yield of plants is enhanced by foliar methyl glucoside

| Compound | % | Plant | Fresh Weight (g) | Fresh Weight (%) | Dry Weight (mg) | Dry Weight (%) |
|---|---|---|---|---|---|---|
| Control | | All Pepper shoots | | 100 | | 100 |
| α-MN | 0.6 | Pepper shoot | 12.5 | 108 | 1390 | 106 |
| urea | 0.3 | Pepper shoot | 13.5 | 117 | 1510 | 115 |
| urea + αMN | | Pepper shoot | 15.2 | 132 | 1720 | 131 |
| α-MN | 0.6 | Pepper shoot | 2.9 | 109 | 370 | 110 |
| Cinnamic + αMN | | Pepper shoot | 3.3 | 126 | 390 | 115 |
| α-MN | 0.6 | Pepper shoot | 2.9 | 109 | 370 | 110 |
| TyClMe | 0.1 | Pepper shoot | 3.2 | 120 | 380 | 113 |
| TyClMe + αMN | | Pepper shoot | 3.4 | 127 | 400 | 119 |
| αMN | 1.9 | Pepper shoot | 2.9 | 98 | 290 | 105 |
| KNO$_3$ | 2.0 | Pepper shoot | 2.8 | 96 | 270 | 99 |
| KNO$_3$ + αMN | | Pepper shoot | 3.1 | 103 | 300 | 108 |
| αMN | 0.6 | Pepper shoot | 2.9 | 109 | 370 | 110 |
| Tyrosine | 0.1 | Pepper shoot | 1.2 | 107 | 120 | 106 |
| Tyrosine + αMN | | Pepper shoot | 0.8 | 115 | 80 | 114 |
| αMN | 1 | Pepper shoot | 2.9 | 98 | 290 | 105 |
| glycine | 0.8 | Pepper shoot | 2.8 | 96 | 280 | 101 |
| glycine + αMN | | Pepper shoot | 3.3 | 110 | 320 | 116 |
| ααβ | 3 | Wheat shoot | | | 44 | 112 |
| KNO$_3$ + (NH$_4$)$_2$SO$_4$ | 0.5 + 0.4 | Wheat shoot | | | 44 | 113 |
| ααβ + KNO$_3$ + (NH$_4$)$_2$SO$_4$ | | Wheat shoot | | | 46 | 117 |
| KNO$_3$ + (NH$_4$)$_2$SO$_4$ | 0.5 + 0.4 | Wheat shoot | .81 | 100 | 13 | 100 |
| PEG + KNO$_3$ + (NH$_4$)$_2$SO$_4$ | 3 + 0.5 + 0.4 | Wheat shoot | .94 | 116 | 14 | 110 |
| ααβ + KNO$_3$ | 1 + 0.5 | Geranium root | | | 7 | 119 |
| ααβ + KNO$_3$ | 1 + 0.5 | Radish root | 1.54 | 110 | 213 | 161 |
| ααβ + KNO$_3$ | 1 + 0.5 | Radish shoot | 11.73 | 127 | 133 | 145 |

Data presented in Table 2, below, compares measures of marketable qualities of plants subjected to various root treatments and untreated controls. Live measurements were taken of plant size including the diameter of whole rosettes and leaf counts. Weekly root treatments of ornamental kale with methyl glucoside plus potassium nitrate grew larger with more leaves than root treatments with separated components or under conventional culture conditions. Six matched replicates were measured for each treatment and control. The first set of measurements was taken two weeks after the onset of treatments, that is, after two weekly applications of 200 ml of solution to drench the roots of each potted plant. Final measurements were taken approximately one month after beginning treatment, that is, after the third treatment was applied to the roots of plants. The root treatments increased the size and leaf count of cabbages by approximately twenty percent.

TABLE 2

Quality of ornamental kale is enhanced by root treatments with methyl glucoside

| Compound | % | Diameter (cm) | Leaf count |
|---|---|---|---|
| Measured at 2 weeks: | | | |
| Untreated Control | | 32.8 | 18.5 |
| ααβ | 3 | 30.9 | 18.8 |
| $KNO_3$ | 0.5 | 34.6 | 19.0 |
| ααβ + $KNO_3$ | 3 + 0.5 | 35.5 | 20.2 |
| Measured at 1 month: | | | |
| Untreated Control | | 32 | 49 |
| ααβ + $KNO_3$ | 3 + 0.5 | 38 | 59 |

Discussion

Active transport of methyl glucosides was evident from leaf tips that became damaged after overdosing root applications. On the other hand, nontoxic concentrations of methyl glucosides enhanced plant growth in a manner consistent with supplemented carbon fixation. Availability of carbon for fixation by plants influences productivity throughout the biosphere. See, I. Fung *Nature* 386:659–660 (1997). Membrane transportability of methyl glucoside may be a key characteristic allowing development of methods for enhancement of plant growth as a result of fixed carbon input. Previous utilization of methyl glucoside as a carbon nutrient for plants has not been reported, possibly, because additives or derivativizations that enhance penetration, metabolism, membrane transport and receptor sites are required for activity. Treatment of roots and shoots proved effective. Root application may be favored because uptake of larger quantities of methyl glucoside are made possible by extended exposure periods as compared to short pulses afforded via the foliar route.

Tyrosine formulated with methyl glucoside increased plant growth. Tyrosine was selected as an additive to methyl glucoside in this study because of its key role in the photosynthetic reaction center (see, J. Wachtveitl, et al., *Biochemistry* 32:10894–10904 (1993)) and because it is a substrate for cyanogenic glucosides in sorghum (see, B. Halkier, et al., *Drug Metabolism and Drug Interactions* 12:285–297 (1995)). Furthermore, glucose transporters such as tyrosine kinase may be induced providing a molecular basis for enhancement. See, e.g., M. Weber, et al., *Fed. Prod.* 43:2246–2250 (1984). On the other hand, hydrophobic amino acids have been shown to inhibit the exit of methyl glucoside out of epithelium into the blood. See, C. Boyd, *J. Physiol.* 294:195–210 (1979). If such a phenomenon occurs in plants, enhancement of turgidity following foliar treatment with tyrosine and methyl glucosides may be due to captive sugars. Gibberellic acid is a candidate for methyl glucoside formulations because it is known to enhance accumulation of tyrosine. See, Y. Hara, et al., *Phytochemistry* 36:643–646 (1994). In order to ascertain that the synergism was not limited to nitrogen nutrient supplementation, trans-cinnamic acid was combined with methyl glucoside. Cinnamic acid proved to be an effective synergist, enhancing growth beyond that stimulated by methyl glucoside alone.

We conclude that methyglucosides provide substrates for plant growth. Other candidates under investigation include (α-methylmannoside, glucoside methylgalactose. See, R. Clayton, et al., *Nature* 387:459–462 (1997). Extra availability of organic carbon increases plant growth (see, e.g., A. Nonomura, et al., *Proc.Natl.Acad.Sci. USA* 89:9794–9798 (1992) and feeding sugar to plants with appropriate mineral nutrient proportioning provides control of growth, specialization and maturation.

The foregoing is illustrative of the present invention and is not to be construed as limiting thereof. The invention is defined by the following claims, with equivalents of the claims to be included therein.

That which is claimed is:

1. A method for regulating the growth of a plant, said method comprising applying to said plant a growth-regulating effective amount of a compound selected from the group consisting of $C_1$–$C_7$ alkyl glucosides, ether derivatives of $C_1$–$C_7$ alkyl glucosides, and combinations thereof.

2. The method according to claim 1, wherein said compound is methyl glucoside.

3. The method according to claim 1, wherein said compound α-methyl glucoside.

4. The method according to claim 1, wherein said compound is β-methyl glucoside.

5. The method according to claim 1, wherein said compound is a combination of α-methyl glucoside and β-methyl glucoside.

6. The method according to claim 1, wherein said compound is PEG-methyl glucoside.

7. The method according to claim 1, wherein said compound is PPG-methyl glucoside.

8. The method according to claim 1, wherein said compound is ethyl glucoside.

9. The method according to claim 1, wherein said compound is propyl glucoside.

10. The method according to claim 1, wherein said compound is applied at a location of said plant selected from the group consisting of root, shoot, stem, one or more leaves, one or more flowers, and fruit.

11. The method according to claim 1, wherein said compound is applied to a root of said plant.

12. The method according to claim 1, wherein said compound is applied to plant tissue selected from the group consisting of cell suspensions, callus tissue cultures, and micropropagation cultures.

13. The method according to claim 1, further comprising the step of applying a fertilizer to said plant.

14. The method according to claim 13, wherein said fertilizer contains elements selected from the group consisting of nitrogen, potassium, phosphorous, calcium, magnesium, sulfur, iron , zinc, copper, cobalt, boron, manganese, molybdenum, and nickle.

15. The method according to claim 13, wherein said fertilizer is a nitrogenous fertilizer.

16. The method according to claim 13, wherein said fertilizer is nitrate or a salt thereof.

17. The method according to claim 13, wherein said compound and said fertilizer are applied simultaneously.

18. The method according to claim 1, wherein said compound is solubilized in an aqueous carrier prior to said step of applying said compound to said plant.

19. The method according to claim 1, further comprising the step of applying a plant growth promoting composition that increases the amount of cytochrome P450 in said plant, said composition comprising:
 (a) a first compound selected from the group consisting of (i) NADPH:cytochrome P450 reductase enzyme and (ii) oxidants that induce NADPH:cytochrome P450 reductase in plants; and
 (b) a second compound selected from the group consisting of (i) cytochrome P450 monooxygenase enzyme and (ii) reductants that induce cytochrome P450 monooxygenase.

20. The method according to claim 13, wherein said fertilizer is ammoniacal nitrogen.

21. A method for treating fruit, said method comprising applying directly to said fruit, a growth regulating effective amount of a compound selected from the group consisting of $C_1$–$C_7$ alkyl glucosides, ether derivatives of $C_1$–$C_7$ alkyl glucosides, and combinations thereof.

* * * * *